United States Patent
Martin et al.

(10) Patent No.: US 10,710,949 B2
(45) Date of Patent: Jul. 14, 2020

(54) COPPER-CONTAINING MULTIMETALLIC CATALYSTS, AND METHOD FOR USING THE SAME TO MAKE BIOBASED 1,2-PROPANEDIOL

(71) Applicant: Archer Daniels Midland Company, Decatur, IL (US)

(72) Inventors: Kevin Martin, Mt. Zion, IL (US); Josh Terrian, Lovington, IL (US); Bethanie Platt, Mt. Zion, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 15/743,347

(22) PCT Filed: Jul. 14, 2016

(86) PCT No.: PCT/US2016/042188
§ 371 (c)(1),
(2) Date: Jan. 10, 2018

(87) PCT Pub. No.: WO2017/011615
PCT Pub. Date: Jan. 19, 2017

(65) Prior Publication Data
US 2018/0201559 A1    Jul. 19, 2018

Related U.S. Application Data

(60) Provisional application No. 62/192,609, filed on Jul. 15, 2015.

(51) Int. Cl.
| | |
|---|---|
| C07C 29/60 | (2006.01) |
| B01J 23/89 | (2006.01) |
| B01J 21/06 | (2006.01) |
| B01J 23/889 | (2006.01) |
| B01J 37/02 | (2006.01) |
| B01J 37/00 | (2006.01) |
| B01J 37/18 | (2006.01) |
| B01J 23/885 | (2006.01) |
| C07C 31/20 | (2006.01) |
| B01J 21/18 | (2006.01) |
| B01J 23/887 | (2006.01) |
| B01J 37/08 | (2006.01) |

(52) U.S. Cl.
CPC .............. *C07C 29/60* (2013.01); *B01J 21/066* (2013.01); *B01J 21/18* (2013.01); *B01J 23/885* (2013.01); *B01J 23/8873* (2013.01); *B01J 23/8892* (2013.01); *B01J 23/8896* (2013.01); *B01J 23/8926* (2013.01); *B01J 23/8953* (2013.01); *B01J 37/0045* (2013.01); *B01J 37/0242* (2013.01); *B01J 37/18* (2013.01); *C07C 31/20* (2013.01); *C07C 31/205* (2013.01); *B01J 37/08* (2013.01)

(58) Field of Classification Search
CPC . B01J 21/066; B01J 21/18; B01J 23/18; B01J 23/885; B01J 23/8873; B01J 23/8892; B01J 23/8896; B01J 23/8926; B01J 23/8953; C07C 31/20; C07C 31/205; C07C 29/60
See application file for complete search history.

(56) References Cited

U.S. PATENT DOCUMENTS

| | | | | |
|---|---|---|---|---|
| 5,037,996 A * | 8/1991 | Suzuki | ................... | C07C 29/149 568/864 |
| 5,391,362 A * | 2/1995 | Reinalda | ................ | B01J 21/066 423/608 |
| 5,543,379 A * | 8/1996 | Gubitosa | .............. | B01J 23/8926 502/184 |
| 6,479,713 B1 * | 11/2002 | Werpy | ..................... | B01J 23/36 568/861 |
| 7,928,148 B2 * | 4/2011 | Bloom | .................... | C07C 29/60 514/738 |
| 2005/0113247 A1 * | 5/2005 | Chen | ........................ | B01J 23/72 502/200 |
| 2007/0207921 A1 * | 9/2007 | Sijpkes | .................. | B01J 23/745 502/338 |
| 2008/0103339 A1 * | 5/2008 | Bloom | .................... | C07C 29/60 568/852 |
| 2014/0309461 A1 * | 10/2014 | Yoshida | ................... | B01J 23/80 568/868 |

* cited by examiner

*Primary Examiner* — Yate' K Cutliff
(74) *Attorney, Agent, or Firm* — William B. Miller

(57) ABSTRACT

Copper-containing, multimetallic catalysts with either a zirconia or carbon support are described which have improved utility for the hydrogenolysis of a glycerol or glycerol-containing feedstock to provide a biobased 1,2-propanediol product. specially, improved carbon-supported examples of such catalysts are described for this reaction as well as for other processes wherein hydrogen is used, with methods for maintaining the activity of these catalysts. Related treatment methods in the preparation of these improved catalysts enable the use of carbons with a desired mechanical strength but which previously lacked activity, for example, for the conversion of a glycerol or glycerol-containing feed to produce 1,2-propanediol, so that copper-containing, multimetallic catalysts may be employed for making a biobased propylene glycol using carbon supports that previously would have not been suitable.

10 Claims, No Drawings

COPPER-CONTAINING MULTIMETALLIC CATALYSTS, AND METHOD FOR USING THE SAME TO MAKE BIOBASED 1,2-PROPANEDIOL

The present application is a national phase application of International Application No. PCT/US2016/042188, filed Jul. 14, 2016, which claims benefit of priority of US Provisional Patent Application No. 62/192609 filed Jul. 15, 2015, the contents of each are incorporated herein by reference.

TECHNICAL FIELD

The present invention relates generally to copper-containing multimetallic catalysts, to methods of using these catalysts, and relates generally also to catalytic methods for producing a biobased propylene glycol especially from a glycerol or glycerol-containing feedstock.

BACKGROUND ART

In recent years, substantial research has been conducted into various catalytic methods for making biobased 1,2-propanediol (commercially known as propylene glycol).

A number of these methods are directed to manufacturing propylene glycol from glycerol, as a means of making productive use of the glycerol produced as a byproduct of making biodiesel, however, a variety of other feedstocks have been converted to propylene glycol as well.

Copper-containing catalysts have been extensively evaluated in many forms for use in these conversions. WO 2014/134733 to Dalal et al. is a recent example of work in the copper-containing catalysts in the field of converting glycerol to propylene glycol, and after reviewing a number of prior art methods involving both homogeneous and heterogeneous catalysts describes a process for the hydrogenolysis of glycerol to produce propylene glycol as the major product, which process comprises reacting the glycerol with hydrogen in the presence of a heterogeneous multicomponent catalyst based on Cu, Zn, Cr and Zr prepared by a co-precipitation method. The multicomponent catalyst was identified for further study after an initial screening of a number of catalysts in certain molar ratios, including Cu:Zn:Ni (3:2:2), Cu:Cr:Ni (3:1:2), Cu:Zn:Cr (3:2:1), Cu:Zn:Cr:Ni (3:2:1:2), Cu:Zn:Cr:Zr (3:4:1:3) and Cu:Zn:Cr:Zr (3:2:1:3).

Interestingly, while Dalal et al. reference prior publications by Chaminand et al. (*Green Chemistry*, 2004, vol. 6, pages 359-361) and Maris et al. (Journal of Catalysis, 2007, vol. 249, pp. 328-337) as support for Dalal's statement that "the Cu/ZnO based catalysts have been reported to give a high catalytic performance for the glycerol dehydroxylation reaction to propylene glycol under mild reaction conditions", on page 359 of Chaminand et al., a CuO-ZnO catalyst was initially selected for evaluation because of its efficiency in the hydrogenolysis of sorbitol to deoxyhexitols, but was found to have low activity and low conversion in glycerol hydrogenolysis (though it was observed to have high selectivity to propylene glycol consistent with the earlier findings of Montassier et al. (Montassier et al., Bulletin de la Societé Chimique de France 1989, No. 2, pp. 148-155) with a Raney copper catalyst).

Balaraju et al., "Selective Hydrogenolysis of Glycerol to 1,2-Propanediol Over Cu—ZnO Catalysts", Catal. Lett., vol. 126, pp. 119-124 (2008) report, however, "high conversion" with "highly selective" Cu—ZnO catalysts under certain conditions at a 50:50 weight ratio of copper to zinc and with small Cu and ZnO particles.

Copper-containing catalyst systems are addressed also in a series of patents assigned to BASF SE, see, e.g., U.S. Pat. Nos. 7,790,937, 8,252,962, 8,273,924 and 8,293,951 all to Henkelmann et al. In U.S. Pat. No. 8,293,951, after reviewing prior references employing various catalysts—Cr-activated copper or cobalt catalysts, nickel, copper-chromium-barium oxide, Raney copper, supported metal catalysts based on Cu, Pd and Rh, copper chromite, copper zinc oxide, copper aluminum oxide, copper silicon dioxide, platinum, cobalt/copper catalysts optionally containing manganese and/or molybdenum—a process is described employing at least three hydrogenation reactors in series with a heterogeneous copper catalyst. The copper catalyst is broadly described, and may additionally comprise at least one further element of "main group I, II, III, IV or V, of transition group I, II, IV, V, VI, VII or VIII and of the lanthanides (IUPAC Groups 1-15 and the lanthanides", col. 18, lines 26-30, though Raney copper and copper alloy-containing catalysts are preferred, particularly those whose metal component consists of copper to an extent of at least 95%, especially to an extent of 99%, col. 18, lines 32-39. Specific combinations of copper with other metals, in oxidic form, reduced elemental form or a combination are also listed, with certain combinations indicated as preferred: Cu (preferred); Cu,Ti (preferred); Cu, Zr; Cu, Mn; Cu, Al (preferred); Cu, Ni, Mn; Cu, Al, at least one other from La (preferred), W, Mo, Mn, Zn (preferred), Ti, Zr, Sn, Ni, Co; Cu, Zn, Zr (preferred); Cu, Cr, Ca; Cu, Cr, C (preferred); and Cu, Al, Mn (preferred) and Zr if appropriate. While very many combinations of other metals are thus indicated in this patent or are mentioned as known from the prior art, this particular patent contains but a single example, using a catalyst composed of the mixed oxides of Cu, Al and La.

SUMMARY OF THE INVENTION

The present invention concerns, in one aspect, a copper-containing multimetallic catalyst comprising copper and one or more additional metals selected from the group consisting of rhenium, palladium, platinum, ruthenium, manganese, and molybdenum on a zirconia or carbon support.

In certain embodiments, the catalyst comprises copper, zinc and one or more additional metals selected from the group consisting of rhenium, palladium, platinum, ruthenium, manganese, and molybdenum or a zirconia or carbon support.

In certain embodiments, the catalyst consists essentially of copper, rhenium and zinc on a zirconia or carbon support.

In certain embodiments, the catalyst consists essentially of copper, palladium and zinc or a zirconia or carbon support.

In certain embodiments, a monoclinic zirconia support is used.

In certain other embodiments, the support is a carbon support having at least one of a) a single pellet crush strength of at least 7.4 MPa and b) a bulk crush strength such that not more than 7.0% of fines are observed to pass through a 40 mesh ASTM sieve upon the application of 3.5 MPa for thirty minutes to a sample of the carbon, together with 5.3% attrition mass loss or less per ASTM D4058, having a surface oxygen group concentration corresponding to a desorption of at least 800 μmol/g combined of carbon monoxide and carbon dioxide through temperature-programmed desorption and analysis with an associated mass spectrometer as described in Figueiredo et al., "Modification of the surface chemistry of activated carbons", *Carbon*, vol. 37, pp. 1379-1389 (1999) and as exemplified herein, and having an alkali metal content of at least 0.5 percent by weight, as measured by inductively coupled plasma analysis.

In certain embodiments where such a carbon support is used, the oxygen content is intrinsic to the carbon support by reason of the organic material from which the carbon has been made and/or the manner in which the carbon has been activated.

In other embodiments, a carbon having the requisite single pellet crush strength is oxidized by exposure to an oxidant to achieve the oxygen content.

In certain embodiments, the carbon support is characterized by an alkali metal content of at least 0.8 percent by weight.

In other embodiments, the carbon support is characterized by an alkali metal content of at least 1 percent by weight.

In other embodiments, the carbon support is characterized by an alkali metal content of not more than 4.8 percent by weight.

In certain other embodiments, the carbon support is characterized by an alkali metal content of not more than 3 percent by weight.

In other embodiments, the carbon support is characterized by an alkali metal content of not more than 2.5 percent by weight.

In other embodiments, the carbon support is characterized by an alkali metal content of not more than 2 percent by weight.

In another aspect, the present invention relates to a method of using a catalyst comprising copper on a carbon support having an surface oxygen group concentration corresponding to a desorption of at least 800 µmol/g combined of carbon monoxide and carbon dioxide through temperature-programmed desorption and analysis with an associated mass spectrometer, in which the catalyst is used to catalyze a chemical process involving hydrogen and wherein the catalyst is treated by exposure to an alkali metal source at least for a time in the carrying out of the process.

In certain embodiments, the catalyst is continuously exposed to an alkali metal source by co-feeding the alkali metal source to a reactor containing the catalyst with a reactant or reactants for the process.

In certain embodiments, the exposure to an alkali metal source is controlled to maintain the alkali metal content of the carbon-supported catalyst within a range of values correlated with an active and stable performance of the catalyst.

In another aspect, the present invention relates to a process for using a copper-containing multimetallic catalyst as described herein for reacting glycerol or a glycerol-containing feed with hydrogen to provide a biobased 1,2-propanediol product.

In certain embodiments, the catalyst is a carbon-supported, copper-containing multimetallic catalyst and the process for using the catalyst to produce a biobased 1,2-propanediol product from a glycerol or glycerol-containing feed includes treating the catalyst by exposure to an alkali metal source during the conversion of the glycerol or glycerol-containing feed to the biobased 1,2-propanediol product.

In certain embodiments, the exposure involves co-feeding the alkali metal source with the glycerol or glycerol-containing feed.

In an embodiment, the exposure involves continuously co-feeding one or more alkali metal salts in solution with the glycerol or glycerol-containing feed.

In certain embodiments, the exposure is controlled to maintain the alkali metal content of the catalyst within the range of 0.5 percent by weight to 4.8 percent by weight.

In certain embodiments, the alkali metal content of the catalyst is maintained in the range of from 0.5 percent by weight to 3 percent by weight.

In certain embodiments, the alkali metal content of the catalyst is maintained in the range of from 0. 8 to 2.5 percent by weight.

In certain embodiments, the alkali metal content of the catalyst is maintained in the range of from 1 to 2 percent by weight.

In certain embodiments, the feed is an aqueous glycerol solution.

In certain embodiments, the feed comprises glycerol and at least one other polyol selected from the five- and six-carbon sugars and sugar alcohols.

DETAILED DESCRIPTION OF EMBODIMENTS

The present invention relates to the discovery of copper-containing, multimetallic catalysts with either a zirconia or carbon support which have improved utility for the hydrogenolysis of a glycerol or glycerol-containing feedstock to provide a biobased 1,2-propanediol product, and especially to the discovery of improved carbon-supported examples of such catalysts for this reaction as well as for other processes wherein hydrogen is used, and further to the discovery of particular methods for maintaining the activity of these carbon-supported, copper-containing multimetallic catalysts in the context of such processes at a given reaction temperature. As well, we have found certain treatment methods may be applied to enable the use of carbons with a desired mechanical strength but which previously lacked activity, for example, for the conversion of a glycerol or glycerol-containing feed to produce 1,2-propanediol, so that copper-containing, multimetallic catalysts may be employed for making a biobased propylene glycol using carbon supports that previously would have not been suitable.

The copper-containing, multimetallic catalysts with either a zirconia or carbon support having improved utility for the hydrogenolysis of glycerol to yield a biobased propylene glycol product (or for the hydrogenolysis of a glycerol-containing feed which may also include one or more additional polyols that can likewise undergo hydrogenolysis to yield propylene glycol, for example, five- and six-carbon sugars and sugar alcohols) comprise copper and one or more additional metals selected from the group consisting of rhenium, palladium, platinum, ruthenium, manganese, and molybdenum. Zinc is present in preferred embodiments for improved selectivity. Of the one or more additional metals, rhenium and palladium are preferred, with palladium being especially preferred.

Thus, in certain embodiments, an hydrogenolysis catalyst of the present invention is a zirconia- or carbon-supported catalyst consisting essentially of copper, rhenium and zinc in oxidic or reduced form. In other embodiments, the catalyst may be a zirconia- or carbon-supported catalyst consisting essentially of copper, palladium and zinc on the support. The metals used in the hydrogenolysis catalysts of the present invention may, in other embodiments, consist only of copper, rhenium or palladium, and zinc on a zirconia or carbon support.

Where zirconia is used as the support for the copper-containing, multimetallic catalysts contemplated herein, preferably a monoclinic zirconia is employed.

Where carbon is used, preferably the carbon will:

a. display good mechanical properties, being characterized by at least one of i) a single pellet crush strength of at least 7.4 MPa and ii) a bulk crush strength such that not more than 7.0% of fines are observed to pass through a 40 mesh ASTM sieve upon the application of 3.5 MPa for thirty minutes to a sample of the carbon, as well as by an attrition mass loss of 5.3 percent or less per ASTM D4058;

b. have a surface oxygen group concentration corresponding to a desorption of at least 800 µmol/g combined of carbon monoxide and carbon dioxide through temperature-programmed desorption and analysis with an associated mass spectrometer as exemplified herein; and c. have an alkali metal content of at least 0.5 percent by weight, as measured by ICP-OES analysis.

U.S. Pat. Nos. 6,479,713 and 6,841,085 (both to Werpy et al.) describe the use of Re-containing multimetallic catalysts. U.S. Pat. No. 6,479,713 utilizes such catalysts for converting a feedstock containing a 5-carbon sugar, sugar alcohol or lactic acid to products including especially propylene glycol, by reaction with hydrogen. U.S. Pat. No. 6,841,085 converts a feed containing a 6-carbon sugar, sugar alcohol or glycerol to products including propylene glycol. The Re-containing catalysts are described as containing at least 0.5 weight percent of rhenium, and as preferably being supported heterogeneous catalysts wherein carbon, zirconia and titania are especially preferred. The catalysts contain at least one other metal, and suitable other metals include Ni, Pd, Ru, Co, Ag, Au, Rh, Pt, Ir, Os and Cu, with Ni, Pd and Ru being described as more preferred and Ni being most preferred. Zinc, however, is not mentioned among the additional metals that could be used in either process, and there is no suggestion that palladium may be used as an alternative rather than as complementary to rhenium in Werpy et al's catalysts.

The copper in certain embodiments may comprise from 1, in other embodiments will be from 3 and in still other embodiments will be from 5 percent by weight on the support (by total weight of the metals and support), up to 8 percent by weight on the support, in other embodiments up to 9 and in still other embodiments will be present at up to 10 percent by weight on the support.

The rhenium or palladium will in certain embodiments comprise at least 0.25 percent by weight of the catalyst (combined metals and support), in other embodiments will comprise at least 0.5 percent by weight of the catalyst, and most preferably will comprise from 1.0 percent up to 2.0 percent by weight of the catalyst.

The zinc according to certain embodiments will comprise from 0.5 percent by weight of the catalyst, in other embodiments will be from 1 percent by weight of the catalyst, and in still other embodiments will comprise from 1.5 percent by weight of the catalyst, up to 2 percent by weight of the catalyst in certain embodiments and in still other embodiments will be present up to 3 percent by weight on the support.

The hydrogenolysis catalysts of the present invention may be made generally as shown in the examples below, by impregnation of the support with a solution of soluble compounds of the selected metals to incipient wetness, drying and reduction under hydrogen at elevated temperatures. Alternatively, impregnation may be with a plurality of solutions containing one or more but not all of the soluble compounds of the selected metals. Preferably, a single mixed solution is used, but if more than one solution is applied, a solution containing the one or more soluble Zn compounds is preferably not applied to the catalyst support before soluble Re/Pd and/or Cu compounds are brought into contact with the support, as applying the Zn first was found in at least one example reported below to result in a less active catalyst for the hydrogenolysis of a glycerol feed.

The hydrogenolysis catalysts of the present invention are useful in a process for making a biobased 1,2-propanediol, by reacting glycerol or a glycerol-containing feed with hydrogen in the presence of the catalyst under suitable reaction conditions.

Parenthetically, by "biobased", we mean those materials whose carbon content is shown by ASTM D6866 to be derived from or based in significant part (at least 20 percent or more) upon biological products or renewable agricultural materials (including but not being limited to plant, animal and marine materials) or forestry materials. "Wholly biobased" thus will be understood as referring to materials whose carbon content by ASTM D6866 is entirely or substantially entirely (for example, 95 percent or more) indicated as of biological origin.

In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

In one embodiment of the process, the feed to the hydrogenolysis process comprises glycerol, especially in the form of an aqueous glycerol solution. In other embodiments, the glycerol can be supplied in solution in an inert, non-aqueous solvent. Non-aqueous solvents that may be used include, but are not limited to, methanol, ethanol, ethylene glycol, propylene glycol, n-propanol, and isopropanol.

A variety of glycerol feedstocks are commercially available in various purities. The purity of United States Pharmacopeia (USP) grade glycerol is greater than 99%. However, the purity of the glycerol having utility in the present invention may be between 10-99% by weight of the feedstock. A commercially available glycerol feedstock produced as a byproduct of biodiesel manufacture contains, in addition to water, other constituents such as triglycerides, free fatty acids, soap stock, salt, and unsaponifiable matter. In one embodiment, the feedstock may comprise 20 to 80% by weight of the glycerol.

In another embodiment, the feed to the hydrogenolysis process comprises glycerol and at least one other polyol selected from the five- and six-carbon sugars and sugar alcohols, which have been found according to U.S. Pat. Nos. 6,479,713 and 6,841,085 to Werpy et al. to also undergo hydrogenolysis to lower polyols inclusive of 1,2-propanediol in the presence of the same catalysts and under the same conditions found effective for the hydrogenolysis of glycerol to produce 1,2-propanediol.

The temperature used in the hydrogenolysis reaction may range from 200 degrees Celsius, especially from 210 degrees Celsius, and more particularly from 225 degrees Celsius up to 250 degrees Celsius, but especially from such temperatures up to 240 degrees Celsius. Hydrogen for the reaction may be supplied at a pressure of from between 2.1 MPa (300 psi), especially from 6.9 MPa (1000 psi) and most especially from 12.4 MPa (1800 psi), up to 13.8 MPa (2000 psi). The liquid hourly space velocity (LHSV), expressed as a volume of reactant per unit volume of catalyst per hour, can range from $0.25\ hr^{-1}$, especially from $0.5\ hr^{-1}$ and more particularly from $0.7\ hr^{-1}$ up to $1.0\ hr^{-1}$.

As previously mentioned, the present invention relates in part to the discovery of improved carbon-supported, copper-containing multimetallic catalysts for the hydrogenolysis of glycerol (or, more generally, of a polyols feed containing one or more of glycerol, a five-carbon sugar, a five-carbon sugar alcohol, lactic acid, a six-carbon sugar or six-carbon sugar alcohol) to provide a biobased propylene glycol product.

We have found, more particularly, that if a carbon support is selected for these copper-containing, multimetallic catalysts which has at least a certain concentration of oxygen-bearing functional groups on its surface (whether intrinsically this is so by virtue of the carbon's source material and/or its manner of activation, or whether the carbon is made to acquire the oxygen-bearing functional groups by an oxidation treatment), and which further contains at least a certain alkali metal content (again, whether intrinsically or by treatment with a source of alkali metal), then provided the copper-containing, multimetallic catalyst made therefrom is exposed in the course of the hydrogenolysis reaction to an alkali metal source, improvements in the catalyst's activity can be realized and sustained through the influence of the in-situ alkali metal exposure as compared to where a carbon is used that possesses the oxygen-bearing functional groups on its surface but not the alkali metal content or that possesses neither the oxygen-bearing functional groups or the alkali metal content.

As a consequence, carbon supports which have desirable mechanical properties, in particular, displaying a desired crush strength and physical durability, but which have heretofore not resulted in copper-containing, multimetallic catalysts with sufficient activity to be used, e.g., in the hydrogenolysis of glycerol to produce a biobased propylene glycol product, now have been modified to be active and useful in that process.

The precise manner in which the alkali metal content and in-situ exposure to an alkali metal source enable the observed improvement in activity is not precisely known, however, we would postulate (without being bound thereby to any particular theory of operation) that the alkali metal content influences both the reducibility and dispersion of the copper on the carbon's surface, perhaps leading to different ratios of copper species in the catalyst and leading to a greater dispersion of copper on the carbon's surface. Temperature programmed reduction testing of 10% Cu/1% Re/2% Zn catalysts with different amounts of sodium included in a carbon extrudate support showed, in this regard, an increased peak temperature of the reduction profile as sodium levels increased. Correspondingly, measurements of copper dispersion percentages and of glycerol breakthrough as a function of time on stream for various 10% Cu/1% Re/2% Zn catalysts with different amounts of sodium included in a commercial carbon nanotube support demonstrated that copper dispersion percentages and the time on stream to glycerol breakthrough increased with the addition of sodium to the support up to a certain point, but declined with the inclusion of greater amounts of sodium.

Based on these findings and having regard particularly for the postulated effects of alkali treatment on these catalysts, we thus expect that while the improved carbon-supported copper-containing, multimetallic catalysts and methods of using described herein have been described with particularity and demonstrated in the specific context of the hydrogenolysis of glycerol and of glycerol-containing feeds to produce 1,2-propanediol, nevertheless, the improved carbon-supported copper-containing, multimetallic catalysts and methods of using the same should be generally of value for other catalytic processes wherein hydrogen is involved.

We observed in this regard in the particular context of the hydrogenolysis of glycerol that the carbon-supported catalysts required at least a certain alkali metal content to become active for the conversion, but that the stability of the catalyst was adversely affected above a certain alkali metal content. We also observed that while significant improvements in activity could be achieved by alkali treatment of a carbon support with good mechanical strength, a low concentration of oxygen functional groups on its surface and also a low alkali content (and that had demonstrated insufficient activity for the conversion absent the alkali treatment), nevertheless the improved activity diminished with continued runtime despite a continuous co-feed of potassium carbonate to the catalyst in situ, indicating that a certain concentration of surface oxygen-functional groups needs to be present for acceptably stable performance. Even in a carbon support with both an intrinsically fairly high concentration of carboxylic acid groups on its surface and an alkali content that was sufficient to provide high activity at the start of a run, however, a diminishment in the performance of the catalyst was likewise observed over time in the absence of exposure to an alkali source in situ or when ongoing exposure to an alkali source in situ was stopped for a time. Yet in the latter instance, when exposure to an alkali source was resumed, the conversion of glycerol increased and progressively returned to its former levels.

Based on these observations, we expect that while the optimum alkali metal content may vary from one process context to the next and that the needed concentration of surface oxygen functional groups and rates of deactivation observed associated with a lower concentration and with not controlling the alkali metal content of the support may likewise vary from one process context to the next, yet a preferred manner of using the carbon-supported, copper-containing, multimetallic catalysts of the present invention in a given process involving the use of hydrogen as a reactant in some fashion will involve a) selecting a suitably mechanically robust carbon support, b) ascertaining whether or not the support intrinsically possesses at least a certain concentration of oxygen functional groups at its surface and, if not, performing an oxidative treatment on the support, c)

ascertaining whether or not the support's intrinsic alkali metal content is sufficient to provide an active catalyst and, if not, performing a treatment of the support with an alkali metal source and d) exposing the catalyst in situ to an alkali metal source in the course of carrying out the process in question, as needed to acceptably maintain the activity of the catalyst.

In this regard, conventionally as a catalyst begins to lose activity over time, the reaction temperature may be adjusted upward from time to time to offset the loss in activity and maintain a desired conversion, though practically speaking, there is a limit to the extent to which losses in catalyst activity can be accommodated by increases in the reaction temperature. We have found, consistent with the observations of the immediately preceding paragraphs, that by the use of a carbon with a certain concentration of surface oxygen functional groups (whether intrinsic to the carbon or supplied by an oxidative treatment) and the use of in situ alkali metal treatment, the activity associated with the alkali metal-containing carbon-supported catalysts of the present invention can be maintained for far longer with accommodating incremental adjustments in the reaction temperature than would otherwise be possible and still stay within an acceptable range of reaction temperatures.

Preferably, the concentration of surface oxygen functional groups and the extent of alkali metal source treatment in the course of carrying out the underlying process will be established to enable a loss of not more than 0.011 percent in conversion on average per hour on stream for a process operating at reaction temperatures within twenty degrees of an initial value, more preferably of not more than 0.005 percent per hour, still more preferably of not more than 0.001 percent per hour and even more preferably of not more than 0.0005 percent per hour.

Where the catalyst's activity and stability are considered together in terms of realizing and maintaining a certain percentage conversion of a feed over a certain time on stream, preferably at least 92 percent of the feed would be able to be converted over a year on stream merely by a judicious co-feeding of alkali metal and without raising the reaction temperature setpoint by more than twenty degrees in that timeframe. More preferably, at least 95 percent of the feed would be able to be converted in this manner, and still more preferably, at least 98 percent of the feed would be able to be converted.

In the particular context of converting a glycerol or glycerol-containing feed to propylene glycol by hydrogenolysis using a carbon-supported, copper-containing multimetallic catalyst, we prefer to use a catalyst consisting of copper, zinc and either of rhenium or palladium on a carbon support having:
a. at least one of i) a single pellet crush strength of at least 7.4 MPa and ii) a bulk crush strength such that not more than 7.0% of fines are observed to pass through a 40 mesh ASTM sieve upon the application of 3.5 MPa for thirty minutes to a sample of the carbon, together with an attrition resistance corresponding to a mass loss of 5.3 percent or less according to ASTM D4058;
b. a surface oxygen group concentration corresponding to a desorption of at least 800 µmol/g combined of carbon monoxide and carbon dioxide through temperature-programmed desorption and analysis with an associated mass spectrometer; and
c. an alkali metal content of at least 0.5 percent by weight, as measured by ICP-OES analysis.

Especially, we prefer that the carbon support be characterized by an alkali metal content (either intrinsic to the carbon, or imparted by an alkali source pretreatment of the carbon support in the synthesis of the catalyst) of from 1 percent by weight to 2 percent by weight, that is maintained through the use of a co-feed of alkali metal compounds solubilized in the feed. Carbonate salts are especially preferred, though those skilled in the art will appreciate that other compounds (for example, acetate salts) could be used, provided of course that salts involving known poisons, such as the chloride and sulfate salts, would not be suggested for use. The examples below demonstrate that co-feeding as little as 100 parts per million by weight of potassium carbonate was quite effective in stabilizing the activity of a carbon-supported, 10 pct. copper/2 pct. rhenium/2 pct. zinc catalyst prepared according to the present invention, using a commercially-available carbon with an alkali metal content (depending on the production lot tested) ranging from 0.8 to 1.5 percent by weight of potassium and having a concentration of oxygen functional groups on its surface estimated by temperature-programmed desorption to be approximately 800 µmol/g, appearing to be mostly in the form of carboxylic acid groups, such that deactivation rates of less than 0.0005 percent per hour were observed over the course of well over a thousand hours runtime on stream.

Where the carbon support as acquired requires a higher concentration of surface oxygen functional species as well as a higher alkali metal content, if the oxidation treatment is to be conducted in the liquid phase, a pretreatment with an oxidant is undertaken first (as illustrated in the examples below) followed by a pretreatment with a source of alkali metal. Both gas and liquid phase oxidations are contemplated, and with a gas phase oxidation it may be possible to perform the oxidation pretreatment following the alkali metal pretreatment.

The following exemplary, non-limiting examples are provided to further describe the embodiments presented herein. Those having ordinary skill in the art will appreciate that variations of these Examples are possible within the scope of the present invention.

EXAMPLES

Examples 1-19

An aliquot of 130 cubic centimeters (155.79 g) of monoclinic zirconia, in the form of 1.6 mm diameter extrudates having a surface area of 55 square meters per gram and a pore volume of 0.30 cubic centimeters per gram (Hg), was placed in a coating drum. A solution was then prepared containing 31.84 grams of $Cu(NO_3)_2 \cdot 3H_2O$, 2.95 grams of 76.5 wt. pct. solution of $HReO_4$ and 7.62 grams of $Zn(NO_3)_2 \cdot 6H_2O$ with sufficient deionized water to have 40 ml of solution, where these numbers are to be understood as based on the weight of the material and the water uptake pour volume. Over the course of thirty minutes, the solution was sprayed onto the zirconia extrudates as they tumbled in the drum coater. The sprayer and solution container were rinsed with approximately 6 ml of deionized water and the rinse water sprayed onto the zirconia as well. The resulting solid at incipient wetness was allowed to tumble for an additional 30 minutes, then dried for 16 hours in an 80 degree Celsius vacuum oven (75 torr pressure). Other catalysts were prepared in an essentially similar manner for comparison with different amounts of the Cu, Re and Zn, on this same zirconia support and on several carbon supports from a single manufacturer, with the exception that the solvent for the metal salts for impregnation of the carbon supports included from 25 to 50 percent of isopropanol to overcome the hydrophobicity of some of the carbon supports (subsequent examples not included in Table 1 did not involve the use of isopropanol unless explicitly noted). As well, in a couple of instances, the metals were incorporated on the support in a sequenced impregnation using a plurality of solutions. In one such instance, a zinc nitrate solution was sprayed onto the support, followed by drying and reduction at 250 degrees Celsius for 4 hours under 5% $H_2$/95% $N_2$, with subsequent impregnation with a mixed copper nitrate-perrhenic acid solution, drying, loading and reduction in situ as described in the following paragraph. In a second such instance, the support was first impregnated with a perrhenic acid solution, then dried and reduced at 250 degrees for 4 hours with 5% $H_2$/95% $N_2$, followed by impregnation with a mixed copper nitrate-zinc nitrate solution, drying, loading and reduction in situ again as described below.

Each of these catalysts was loaded into a 30 cubic centimeter reactor. The loaded catalyst was reduced by 5 percent hydrogen flow according to the following protocol: ramp at 2 degrees Celsius per minute to 200 degrees Celsius under hydrogen flow and hold for 6 hours; then ramp to 250 degrees Celsius at 2 degrees Celsius per minute, holding at 250 degrees for from 16-20 hours; then cooling to 60 degrees Celsius under continued hydrogen flow. The catalysts so prepared were then evaluated at various pressures using supplied hydrogen, at various reaction temperatures, various hydrogen flowrates and various liquid hourly space velocities of a supplied 80 percent by weight solution of glycerol in water, by establishing the reaction pressure with hydrogen, washing with water at an LHSV of from 1-2 $hr^{-1}$ for from 4-16 hours, switching to the glycerol/water feed solution and ramping the reactor temperature up to a desired temperature at 5 degrees Celsius per minute. Periodic liquid samples were analyzed by HPLC and GC.

The results are shown in Table 1 as follows, where C-1, C-2, C-3 etc. are indicative of different carbon supports:

Example 20

A catalyst comprised of 5% Cu, 1% Re and 1% Zn on the same monoclinic zirconia support was prepared as in Examples 1-19, loaded into the 30 cubic centimeter reactor and reduced for evaluation, with the reduction method being slightly modified, however, from the method used in Examples 1-19, for this and for all subsequent examples.

More particularly, for this and subsequent examples, the loaded catalyst was reduced according to the following protocol: ramp at 2 degrees Celsius per minute to 250 degrees Celsius under 1000 ml/min of 5% hydrogen and hold for 1 hour; then switch to 100% hydrogen and continue holding for 3 more hours at 250 degrees Celsius; then cooling to 60 degrees Celsius under continued hydrogen flow. After cooling, the reactor is pressurized to the appropriate pressure and a flow of deionized water is started with 1000 ml/min of hydrogen at an LHSV of 1 $hr^{-1}$ for 16 hours. The deionized water is then switched to the glycerol-containing feed and flow is continued for 4 hours before the reactor is heated to the desired reaction temperature.

The specific reaction conditions employed for the evaluation of the catalyst in this example were a reaction temperature of 210 degrees Celsius, a pressure of 12.4 MPa, gauge (1800 psig), an LHSV of 0.7 $hr^{-1}$, and a hydrogen flow rate of 2000 cubic centimeters per minute (at standard temperature and pressure conditions). Samples were regularly taken over a 6480 hour run, and the average results indicated for different intervals of the run are shown in Table 2 as follows:

TABLE 2

| TOS (hrs) | Conv. % | Yield, wt % | Molar Sel., % | Productivity, g/liter cat/hr |
|---|---|---|---|---|
| 0-1000 | 99.91 | 74.70 | 90.49 | 418.34 |
| 1000-2000 | 99.85 | 78.45 | 95.09 | 439.34 |
| 2000-3000 | 99.63 | 80.46 | 97.74 | 450.60 |
| 3000-4000 | 99.26 | 79.92 | 97.44 | 447.55 |
| 4000-5000 | 98.66 | 79.87 | 97.98 | 447.27 |
| 5000-6500 | 97.89 | 78.53 | 97.09 | 439.76 |
| Average | 99.20 | 78.66 | 95.97 | 440.47 |

TABLE 1

| Catalyst | Support | Temp, ° C. | Pressure MPa (g) | LHSV $hr^{-1}$ | $H_2$ cc/min | Conv. % | PG Yield % | Molar Sel. % | Productivity (g/liter cat/hr) |
|---|---|---|---|---|---|---|---|---|---|
| 1% Zn, then 5% Cu/1% Re | Zr | 215 | 12.4 | 0.50 | 2000 | 76.38 | 58.02 | 91.97 | 232.1 |
| 1% Re, then 5% Cu/1% Zn | Zr | 210 | 12.4 | 0.70 | 2500 | 98.74 | 73.59 | 90.20 | 412.1 |
| 5% Cu/1% Re/1% Zn | Zr | 211 | 12.8 | 0.70 | 2010 | 99.11 | 78.61 | 96.01 | 440.2 |
| 5% Cu/1% Re/0.5% Zn | Zr | 215 | 12.4 | 0.50 | 2000 | 96.63 | 66.10 | 82.86 | 264.4 |
| 5% Cu/1% Re/1% Zn | Zr | 216 | 13.6 | 0.42 | 2000 | 97.77 | 75.16 | 93.08 | 253.4 |
| 5% Cu/1% Re/1.5% Zn | Zr | 2100 | 12.4 | 0.67 | 2000 | 93.16 | 70.84 | 92.00 | 381.3 |
| 5% Cu/1% Re/2% Zn | Zr | 215 | 12.4 | 0.64 | 2000 | 99.02 | 75.17 | 91.89 | 385.9 |
| 5% Cu/1% Re/3% Zn | Zr | 224 | 12.4 | 0.50 | 2000 | 97.72 | 76.80 | 95.13 | 307.2 |
| 5% Cu/1% Re/1% Zn | Zr | 215 | 12.4 | 0.50 | 2000 | 96.03 | 70.95 | 89.49 | 283.8 |
| 5% Cu/0.25% Re/1% Zn | Zr | 210 | 12.4 | 0.7 | 2500 | 96.72 | 78.15 | 97.78 | 437.6[a] |
| 5% Cu/0.5% Re/1% Zn | Zr | 210 | 12.4 | 0.7 | 2500 | 96.70 | 78.79 | 98.62 | 441.2 |
| 5% Cu/1% Re/1% Zn | C-1 | 229 | 12.3 | 0.41 | 1995 | 94.60 | 77.70 | 99.39 | 252.1 |
| 5% Cu/1% Re/1% Zn | C-2 | 225 | 8.3 | 0.43 | 2000 | 71.89 | 58.25 | 98.01 | 198.1 |
| 5% Cu/1% Re/1% Zn | C-3 | 226 | 12.2 | 0.40 | 1999 | 86.46 | 70.89 | 99.27 | 229.7 |
| 10% Cu/2% Re/2% Zn | C-3 | 226 | 12.3 | 0.70 | 2043 | 97.51 | 78.97 | 98.01 | 442.2 |
| 5% Cu/1% Re/1% Zn | C-4 | 226 | 11.6 | 0.40 | 1998 | 55.70 | 47.44 | 103.07 | 151.8 |
| 5% Cu/1% Re/1% Zn | C-5 | 229 | 12.0 | 0.40 | 1980 | 84.72 | 70.22 | 100.35 | 224.7 |
| 5% Cu/1% Re/1% Zn | C-5 | 224 | 12.2 | 0.70 | 1998 | 95.87 | 78.02 | 98.49 | 436.9 |
| 10% Cu/1% Re/2% Zn | C-6 | 230 | 12.4 | 0.40 | 2000 | 84.95 | 67.66 | 96.38 | 216.5 |

[a]Catalyst showed good performance, but upon removal from the reactor a significant amount of copper sol was suspended in the solution.

Comparative Example 1

During the course of the run reported in Example 20, an analysis was undertaken for the byproduct polyols that have been reported for other glycerol hydrogenolysis catalytic processes. Meanwhile, a Ni/Re carbon-supported catalyst of the type employed for the 30 cubic centimeter bed flow reactor examples in U.S. Pat. No. 6,479,713 to Werpy et al. was evaluated for the production of byproduct polyols, under the preferred conditions specified in the '713 patent. The results for these two catalysts are reported below in Table 3, where all selectivities reported are molar percent selectivities:

TABLE 3

| Catalyst | Conv. % | Yield Wt % | PG Sel., % | EG Sel., % | 2,3-BDO Sel., % | 2,3-PeDO Sel., % | Productivity g/liter/hr |
|---|---|---|---|---|---|---|---|
| 5% Cu/1% Re/1% Zn | 99.20 | 78.66 | 95.97 | 1.43 | <0.01 | 0.05 | 440.5 |
| Ni/Re (on C) | 86.00 | 66.49 | 93.56 | 4.31 | 0.44 | 0.06 | 186.2 |

Comparative Examples 2 and 3

A catalyst comprised of 10% Cu, 1% Re and 2% Zn on a commercially available steam activated, acid washed carbon extrudate in the form of a 0.8 mm diameter pellet (Norit ROX 0.8 activated carbon) was prepared, loaded into the 30 cubic centimeter reactor and reduced for evaluation in the same manner as in Example 20.

This carbon had shown good activity as a support for glycerol hydrogenolysis with a Ni/Re catalyst, and possessed good mechanical stability, being characterized by a) an average single pellet crush strength of 14.7 MPa (1500 grams per square millimeter on average, as determined using a TA XTPlus® Texture Analyzer with a 1 millimeter, TA-45 incisor knife blade to cleave the extrudate pellet across its cross-section (Texture Technologies Corporation, Hamilton, Mass.)), b) a bulk crush strength such that just 3.7 percent of fines were created that passed through a 40 mesh (420 μm) ASTM sieve, through the application of a load of 3.5 MPa over the course of thirty minutes to about 49 mL of carbon in a 50 mL graduated cylinder by means of a TA-49 round plunger and single ball bearing in the same Texture Technologies XTPlus® Texture Analyzer, and c) an attrition mass loss rate of 5.3 percent by weight according to ASTM D4058.

ASTM D4058 specifies that a representative sample of about 110 grams of the material to be tested is first obtained with gentle handling by splitting or quartering, the sample is gently sieved an a No. 20 (850 μm) ASTM sieve, the presieved sample is transferred to a widemouthed container tared to the nearest 0.01 g, and then an activated carbon sample is to be air-dried for 4 hrs at 190 degrees Celsius (though we dried our carbon supports at 120 degrees Celsius as a precaution against burning). The dried sample is cooled for at least 30 minutes in a desiccator using freshly regenerated (at 220-260 deg C) molecular sieves as the desiccant, and 100 grams of the cooled carbon (weighed to the nearest 0.01 g) is transferred from the desiccator into a 254 mm ID, 152 mm long lidded test cylinder with a 51 mm tall straight plate baffle extending the length of the test cylinder. After 1800 revolutions at 60±5 rpm, the test cylinder is rotated until the baffle is at the top, and the test cylinder is tapped several times with a rubber mallet to allow the fines generated by attrition to collect at the bottom of the test cylinder. The cylinder's contents are emptied onto a No. 20 ASTM sieve, using a fine bristle brush to clean out the test cylinder and its cover onto the sieve. The sieve is gently agitated by hand, and the fines collected in the pan under the sieve are dried in the same manner as originally, then weighed to the nearest 0.1 g and compared to the weight of carbon transferred from the desiccator to the test cylinder to determine the attrition mass loss number.

In terms of alkali metal content and its concentration of surface oxygen functional groups, however, this carbon had an unmodified (original) sodium content of 1282 mg/kg and a potassium content of 367 mg/kg and a surface oxygen functional group concentration by temperature-programmed desorption of 489 μmol/g (distributed between 114 μmol/g of functional groups leading to the desorption of carbon dioxide and 375 μmol/g of functional groups leading to the desorption of carbon monoxide).

The reaction conditions were a reaction temperature of 213 degrees Celsius, a pressure of 12.7 MPa, gauge (1847 psig), an LHSV of 0.5 hr$^{-1}$, and a hydrogen flow rate of 2000 cubic centimeters per minute (at standard temperature and pressure conditions) to provide a hydrogen:glycerol molar feed ratio of 43:1.

Only 7.3 percent of the glycerol was converted after 40 hours on stream, with a selectivity of propylene glycol of 95.7 percent and corresponding yield of 5.8 percent of propylene glycol. A second run was then conducted on the same catalyst at a higher temperature of 232 degrees Celsius in an attempt to boost the catalyst's activity, at a pressure of 4.5 MPa, gauge (650 psig), an LHSV of 0.5 hr$^{-1}$ and the same hydrogen:glycerol feed ratio of 43:1, with now 55.9 percent conversion of the glycerol but a reduced selectivity to propylene glycol of 86.2 percent and a percentage yield of 39.8 percent to the desired propylene glycol product.

Examples 21-23

A series of catalysts were prepared for evaluation in the same 30 cubic centimeter reactor and according to the same procedure as employed in Example 20, with each catalyst using 10% Cu, 1 to 2% Re and 2% zinc on the same ROX 0.8 carbon extrudate as the support, but with, however, different pretreatments being performed on the carbon support.

In one instance, the carbon was oxidized in the liquid phase with a 30 percent aqueous solution of hydrogen peroxide, by adding 100 mL of the extrudate pellets to a 500 mL beaker and then slowly adding 200 mL of the hydrogen peroxide solution at room temperature over the course of about thirty minutes. The mixture was then stirred with a magnetic stir bar for 1 hour. No heat was added and the temperature was not monitored or controlled. The carbon was then vacuum-filtered using a glass-fritted Buchner funnel, and the filtered extrudates were rinsed five times with 100 mL aliquots of deionized water at room temperature. Following drying in a shallow pan in a 125 degrees Celsius forced-air oven, a sample was analyzed and showed an increase in the total concentration of surface oxygen functional groups from 489 µmol/g to 968 µmol/g, of which 248 µmol/g was associated with functional groups leading to the desorption of carbon dioxide and 720 µmol/g was associated with functional groups leading to the desorption of carbon monoxide.

In another instance, another portion of the carbon was treated with an alkali metal source in the liquid phase, in the form of a potassium hydroxide solution, by combining the extrudates with 200 mL of 2.5 weight percent potassium hydroxide in a beaker with stirring for thirty minutes at room temperature. The extrudates were then vacuum-filtered through a 20 µm filter and dried overnight in a shallow pan in the same 125 degrees Celsius forced-air oven.

In another example, the carbon was first oxidized in the liquid phase with an aqueous nitric acid solution, by combining 100 mL of the carbon extrudates with 100 mL of 5M nitric acid in a 250 mL round bottom flask equipped with a water-cooled condenser and situated in a silicone oil bath. The mixture was heated to 105 degrees Celsius with stirring, and allowed to react over 220 minutes. The flask was then removed from the oil bath and allowed to cool to room temperature, with the contents then being vacuum-filtered using a glass-fritted Buchner funnel. After rinsing the filtered extrudates with five 100 mL aliquots of deionized water at room temperature, a portion was set aside for drying and analysis, while the remaining extrudates then were treated by exposure to potassium hydroxide in the same manner as just described above.

By means of the sequential oxidation with nitric acid and treatment with potassium hydroxide, an increase in the total concentration of surface oxygen functional groups from 489 µmol/g to 5056 µmol/g, of which 2092 µmol/g was associated with functional groups leading to the desorption of carbon dioxide and 2964 µmol/g was associated with functional groups leading to the desorption of carbon monoxide, while ICP-OES analysis of the nitric acid (only) treated carbon sample and of the nitric acid- and potassium hydroxide-treated carbon extrudates showed the following results (where all concentrations are reported in mg/kg):

|  | Cl | Al | P | S | Zn | Co | Ni | Fe | Cr | Mg | Ca | Cu | Na | K | Mn | Mo | B |
|---|---|---|---|---|---|---|---|---|---|---|---|---|---|---|---|---|---|
| 5M Nitric | 15.13 | 271 | 6.94 | 1993 | 8.04 | ND | 1.04 | 117 | 1.56 | 78.9 | 97.8 | 4.69 | 179 | 176 | 11.8 | ND | 17.4 |
| 5M Nitric + 2.5% KOH | 116.28 | 346 | 4.62 | 2241 | 2.13 | ND | 1.16 | 141 | 1.92 | 95.7 | 112 | 4.77 | 387 | 46980 | 14.2 | ND | 5.87 |

The results observed with the catalysts prepared from these various carbons are shown in Table 4 as follows, where a consistent liquid hourly space velocity of 0.5 hr$^{-1}$ and hydrogen:glycerol molar feed ratio of 43:1 were used:

TABLE 4

| Treatment | TOS (hrs) | Temp. (deg. C.) | Pressure (MPa, gauge) | Conversion (%) | PG Molar Selectivity (%) | PG Yield (%) |
|---|---|---|---|---|---|---|
| None | 40 | 213 | 12.7 | 7.3 | 95.7 | 5.8 |
| None | 160 | 232 | 4.5 | 55.9 | 86.2 | 39.8 |
| H$_2$O$_2$ | 88 | 224 | 12.4 | 78.7 | 98.6 | 64.1 |
| KOH | 40 | 225 | 12.4 | 100.0 | 95.0 | 78.5 |
| Nitric acid/ KOH | 80 | 225 | 12.4 | 99.5 | 96.2 | 79.1 |

Example 24

A 10% Cu/2% Re/2% Zn catalyst was prepared as in previous examples on a commercially available granular carbon with good mechanical properties, in common with the Norit ROX 0.8 carbon used in Examples 21-23, but also with a higher intrinsic alkali metal content and a higher concentration of surface oxygen functional groups.

The carbon in question, Jacobi GA AddSorb series activated carbon (Jacobi Carbons, Inc., Columbus Ohio), more particularly was found to contain 523 mg/kg of sodium and 14,010 mg/kg of potassium (compared to a total alkali metal content for the ROX 0.8 carbon of 1659 mg/kg), a combined surface oxygen functional group concentration of 821 µmol/g (391 µmol/g from functional groups reflected by desorbed CO$_2$ and 430 µmol/g from functional groups associated with the desorption of carbon monoxide), possessed a bulk crush strength such that just 3.6 percent of fines were created that passed through a 40 mesh ASTM sieve through the application of a load of 3.5 MPa over the course of thirty minutes in the same apparatus as described in Comparative Examples 2 and 3, and exhibited an attrition mass loss rate of 0.4 weight percent according to ASTM D4058.

The resultant catalyst was then evaluated in the same 30 cubic centimeter reactor, with an 80 percent glycerol/20 percent deionized water feed supplied along with hydrogen at a hydrogen:glycerol molar feed ratio again of 43:1, an LHSV of 0.5 hr$^{-1}$ and at a pressure of 10.4 MPa, gauge (1500 psig). No oxidation or alkali metal source pretreatment was undertaken of the Jacobi GA carbon before the Cu, Re and Zn metals were deposited thereon, and initially there was no exposure in situ from an alkali metal source in the course of the hydrogenolysis reaction. At a reaction temperature of 225 degrees Celsius, the observed glycerol conversion over 1024 hours on stream was 99.7 percent and the percentage molar yield was 80.1 percent. The deactivation rate was observed to be increasing slightly, however, so that from time to time the reaction temperature was increased slightly to maintain the conversion and yield, as shown below in Table 5. After increasing the reaction temperature in this manner from 225 degrees Celsius to 238 degrees Celsius, a co-feed of 250 parts per million by weight of K$_2$CO$_3$ was begun, and the reaction temperature was able to be reduced while still maintaining high glycerol conversion over the catalyst.

TABLE 5

| TOS range, hrs | Feed Additive | Temp, deg. C. | Conversion % | Molar Yield % |
|---|---|---|---|---|
| 0-1024 | None | 225 | 99.7 | 80.1 |
| 1064-1304 | None | 228 | 99.6 | 81.4 |
| 1376-1656 | None | 230 | 99.8 | 81.0 |
| 1680-1984 | None | 233 | 99.8 | 80.4 |
| 2384-2552 | None | 235 | 99.5 | 80.2 |
| 2600-2936 | None | 238 | 99.6 | 78.5 |
| 2952-3192 | 250 ppm K$_2$CO$_3$ | 236 | 99.9 | 79.8 |

TABLE 5-continued

| TOS range, hrs | Feed Additive | Temp, deg. C. | Conversion % | Molar Yield % |
|---|---|---|---|---|
| 3264-3688 | 250 ppm K$_2$CO$_3$ | 235 | 99.4 | 79.3 |
| 3880-4144 | 250 ppm K$_2$CO$_3$ | 233 | 99.3 | 79.5 |

To demonstrate this effect further, a fresh sample of the same 10% Cu/2% Re/2% Zn on Jacobi GA carbon catalyst was loaded into the 30 cc reactor and evaluated with a co-feed of 100 ppm of potassium carbonate with the 80 percent glycerol feed, at the same pressure and same hydrogen:glycerol feed ratio, for 1500 hours runtime. Very stable reactor performance was observed, with a deactivation rate considerably less than 0.0005 percent conversion loss per hour. After about 1500 hours, the co-feed was stopped, and in the absence of compensating temperature increases the conversion dropped within 170 hours to about 91.5 percent from 100 percent. After the co-feed was restarted, the conversion steadily increased and approached the levels realized before the co-feed was stopped, as shown below in Table 6.

TABLE 6

| TOS range, hrs | Feed Additive | Temp, deg. C. | Conversion % | Molar Yield % |
|---|---|---|---|---|
| 512-1505 | 100 ppm K$_2$CO$_3$ | 220 | 99.8 | 81.0 |
| 1532 | None | 220 | 100.0 | 80.3 |
| 1656 | None | 220 | 99.6 | 80.3 |
| 1680 | None | 220 | 94.4 | 76.2 |
| 1704 | 100 ppm K$_2$CO$_3$ | 220 | 91.5 | 74.0 |
| 1728 | 100 ppm K$_2$CO$_3$ | 220 | 93.3 | 76.0 |
| 1744 | 100 ppm K$_2$CO$_3$ | 220 | 94.8 | 76.8 |
| 1768 | 100 ppm K$_2$CO$_3$ | 220 | 96.1 | 78.5 |
| 1792 | 100 ppm K$_2$CO$_3$ | 220 | 96.7 | 79.2 |

Examples 25-32

For these examples, a series of catalysts were prepared on the Jacobi GA carbon using 10% by weight of Cu (as copper nitrate trihydrate), 1% by weight of Zn (as zinc nitrate hexahydrate) and 1% by weight of each of Rh (as rhodium nitrate), Pt (as dihydrogen hexachloroplatinate hexahydrate (1$^{st}$ Pt entry) and platinum (IV) nitrate (2$^{nd}$ Pt entry)), Pd (palladium nitrate), Ru ruthenium nitrosylnitrate), Mn (manganese nitrate) and Mo (potassium molybdate(IV)), for screening various other combinations of metals and to assess the initial activity and selectivity of the catalysts prepared therefrom for the hydrogenolysis of a glycerol-containing feed to produce propylene glycol. 400 milligram charges of each of the catalysts were loaded into parallel, microscale high throughput reactors and evaluated for the hydrogenolysis of the same 80 percent glycerol/20 percent deionized water feed (but with no potassium carbonate co-feed). As per conventional practice, the reaction conditions were selected to clearly illustrate differences in performance between the various catalysts screened, rather than for optimal performance of any given catalyst. The reaction temperature was set at 225 degrees Celsius, with 6.2 MPa, gauge (800 psig) hydrogen being supplied for the hydrogenolysis (with a 2 hour hold time and 500 rpm orbital shaking for thorough agitation and gas/solid/liquid contact). The results are shown in Table 7 as follows, and demonstrate that all of the catalysts are active for carrying out the hydrogenolysis reaction:

TABLE 7

| Catalyst | Conversion (%) | Molar Yield (%) | Selectivity to PG (%) |
|---|---|---|---|
| 10Cu:1Zn:1Pd | 41.6 | 23.6 | 68.6 |
| 10Cu:1Zn:1Pt | 21.9 | 12.8 | 70.7 |
| 10Cu:1Zn:1Pt | 51.1 | 25.1 | 59.5 |
| 10Cu:1Zn:1Rh | 42.8 | 22.9 | 64.8 |
| 10Cu:1Zn:1Ru | 40.1 | 20.7 | 62.3 |
| 10Cu:1Zn:1Mn | 43.4 | 24.2 | 67.3 |
| 10Cu:1Zn:1Mo | 43.8 | 23.5 | 64.8 |

Example 33

A more extended and larger-scale evaluation was conducted of a 10% Cu/1% Pd/2% Zn on Jacobi GA carbon catalyst in the same 30 cubic centimeter reactor and at a jacket temperature ranging from 212 degrees Celsius to 227 degrees Celsius, an LHSV of 0.5 hr$^{-1}$, a hydrogen:glycerol molar feed ratio of 43:1 and a 12.4 MPa, gauge pressure (1800 psig), by virtue of the added hydrogen. The feed was again a combination of 80 percent glycerol and 20 percent water, with a 250 parts per million by weight co-feed of potassium carbonate. Over the course of 1200 hours on stream, the catalyst converted on average 99.1 percent of the glycerol in the feed at an average selectivity to propylene glycol of 99.4 percent and an average molar yield of 81.4 percent. The deactivation rate over this time was about 0.0008 percent conversion loss per hour, at an average compensating reaction temperature increase of 0.0056 degrees Celsius per hour to partially offset the conversion losses experienced over the 1200 hours on stream.

The invention has been described with reference to certain exemplary embodiments, compositions and uses thereof. However, it will be recognized by those of ordinary skill in the art that various substitutions, modifications, or combinations of any of the exemplary embodiments may be made without departing from the spirit and scope of the disclosure. Thus, the disclosure is not limited by the description of the exemplary embodiments, but rather by the appended claims as originally filed.

What is claimed is:

1. A process, comprising reacting a glycerol or glycerol-containing feed with hydrogen in the presence of a catalyst comprising copper, zinc and one or more additional metals selected from the group consisting of rhenium, palladium, platinum, ruthenium, manganese, and molybdenum on a zirconia or carbon support to produce a biobased 1,2-propanediol, wherein when a carbon support is used, the carbon has a surface oxygen group concentration corresponding to a desorption of at least 800 µmol/g combined of carbon monoxide and carbon dioxide through temperature-programmed desorption and analysis with an associated mass spectrometer, and treating the catalyst in the course of reacting the glycerol or glycerol-containing feed with hydrogen by exposure to an alkali metal source.

2. The process of claim 1, further comprising establishing a reaction temperature set point for the process and determining an initial conversion of the glycerol or glycerol-containing feed at that reaction temperature set point, and further wherein treating the catalyst by exposure to an alkali metal source involves co-feeding an alkali metal source with the glycerol or glycerol-containing feed to a sufficient extent that the catalyst experiences not more than 0.011 percent loss in conversion from the initial conversion on average per hour on stream while the reaction temperature is maintained within twenty degrees of the reaction temperature set point.

3. The process of claim 2, wherein an alkali metal source is co-fed to a sufficient extent such that the catalyst experiences not more than 0.005 percent loss in conversion from the initial conversion on average per hour on stream while the reaction temperature is maintained within twenty degrees of the reaction temperature set point.

4. The process of claim 2, wherein an alkali metal source is co-fed to a sufficient extent such that the catalyst experiences not more than 0.001 percent loss in conversion from the initial conversion on average per hour on stream while the reaction temperature is maintained within twenty degrees of the reaction temperature set point.

5. The process of claim 2, wherein an alkali metal source is co-fed to a sufficient extent such that the catalyst experiences not more than 0.0005 percent loss in conversion from the initial conversion on average per hour on stream while the reaction temperature is maintained within twenty degrees of the reaction temperature set point.

6. The process of claim 1, further comprising establishing a reaction temperature set point for the process and determining an initial conversion of the glycerol or glycerol-containing feed at that reaction temperature set point, and further wherein treating the catalyst by exposure to an alkali metal source involves co-feeding the alkali metal source with the glycerol or glycerol-containing feed to a sufficient extent that at least 92 percent of the glycerol in the feed over the course of a year on stream is converted without replacing the catalyst and while the reaction temperature is maintained within twenty degrees of the reaction temperature set point.

7. The process of claim 6, wherein an alkali metal source is co-fed to an extent such that at least 95 percent of the glycerol in the feed over the course of a year on stream is converted without replacing the catalyst and while the reaction temperature is maintained within twenty degrees of the reaction temperature set point.

8. The process of claim 6, wherein an alkali metal source is co-fed to an extent such that at least 98 percent of the glycerol in the feed over the course of a year on stream is converted without replacing the catalyst and while the reaction temperature is maintained within twenty degrees of the reaction temperature set point.

9. The process of any one of claim 1 or 2-8, wherein the catalyst used therein is carbon-supported and wherein the carbon support has:

- at least one of a) a single pellet crush strength of at least 7.4 MPa and b) a bulk crush strength such that not more than 7.0 percent of fines are observed to pass through a 40 mesh ASTM sieve upon the application of 3.5 MPa for thirty minutes to a sample of the carbon;
- a 5.3 percent or lower attrition mass loss according to ASTM D4058; and
- an alkali metal content of at least 0.5 percent by weight, as measured by ICP-OES analysis.

10. The process of claim 9, wherein by the exposure of the catalyst to an alkali metal source, the alkali metal content of the support is maintained in a range of from 0.5 percent by weight to 4.8 percent by weight.

\* \* \* \* \*